United States Patent
Wilhelm et al.

(10) Patent No.: US 9,512,167 B2
(45) Date of Patent: Dec. 6, 2016

(54) OPTIMIZED SYNTHESIS OF PURE, NON-POLYMORPHIC, CRYSTALLINE BILE ACIDS WITH DEFINED PARTICLE SIZE

(75) Inventors: Rudolf Wilhelm, Bischweier (DE); Markus Proels, Freiburg (DE); Erik Fischer, Vaerlose (DK); Heidi Waenerlund Poulsen, Bagsvaerd (DK)

(73) Assignee: Dr. Falk Pharma GmbH, Freiburg (DE)

( * ) Notice: Subject to any disclaimer, the term of this patent is extended or adjusted under 35 U.S.C. 154(b) by 500 days.

(21) Appl. No.: 13/989,012

(22) PCT Filed: Nov. 30, 2011

(86) PCT No.: PCT/EP2011/071406
§ 371 (c)(1),
(2), (4) Date: Aug. 6, 2013

(87) PCT Pub. No.: WO2012/072689
PCT Pub. Date: Jun. 7, 2012

(65) Prior Publication Data
US 2014/0050791 A1  Feb. 20, 2014

(30) Foreign Application Priority Data
Nov. 30, 2010 (EP) .................... 10193143

(51) Int. Cl.
*A61K 31/575* (2006.01)
*C07J 9/00* (2006.01)
*C07J 7/00* (2006.01)

(52) U.S. Cl.
CPC ............... *C07J 7/008* (2013.01); *C07J 9/005* (2013.01); *C07B 2200/13* (2013.01); *Y10T 428/2982* (2015.01)

(58) Field of Classification Search
CPC ............... C07J 9/005; C07B 2200/13; Y10T 428/2982

USPC ........................... 552/553; 514/182
See application file for complete search history.

(56) References Cited

U.S. PATENT DOCUMENTS

| 5,512,558 A | 4/1996 | Enhsen et al. |
| 2010/0311708 A1 | 12/2010 | Moustafa et al. |

FOREIGN PATENT DOCUMENTS

| EP | 0 624 595 A2 | 11/1994 |
| EP | 1 317 925 A1 | 11/2003 |
| WO | WO 2009/013334 A1 | 1/2009 |

OTHER PUBLICATIONS

PCT/EP2011/071406—International Search Report, Feb. 8, 2012.
PCT/EP2011/071406—International Written Opinion, Feb. 8, 2012.
PCT/EP2011/071406—International Preliminary Report on Patentability, Jun. 4, 2013.
Batta, Askok K., "A Convenient Synthesis Of Dinorbile Acids: Oxidative Hydrolysis Of Norbile Acid Nitriles", Steroids, May 9, 1999, vol. 64, No. 11, pp. 780-784, Elsevier Science Publishers, New York, NY, US.
Halilbasic, Emina, "Side Chain Structure Determines Unique Physiologic And Therapeutic Properties Of norUrsodeoxycholic Acid in Mdr2–/– Mice", Hepatology, Jun. 1, 2009, vol. 49, No. 6, pp. 1972-1981, Wiley, US.
Schteingart, Claudio, "Synthesis Of 24-Nor-5.Beta.-Cholan-23-Oic Acid Derivatives: A Convenient And Efficient One-Carbon Degradation Of The Side Chain Of Natural Bile Acids", Journal of Lipid Research, Jan. 1, 1988, vol. 29, No. 10, pp. 1387-1395, American Society for Biochemistry and Molecular Biology, Inc, US.

*Primary Examiner* — Barbara P Badio
(74) *Attorney, Agent, or Firm* — Curatolo Sidoti Co., LPA; Salvatore A. Sidoti; Floyd Trillis, III

(57) ABSTRACT

The present invention relates to a pure polymorph of Nor-UDCA or Bis-nor-UDCA, or of a pharmaceutically acceptable salt thereof. The invention further provides a pharmaceutical composition comprising the polymorph of the invention, and a method for preparing the polymorph. The invention includes the pharmaceutical use of the polymorph or of the pharmaceutical composition of the invention.

20 Claims, 5 Drawing Sheets

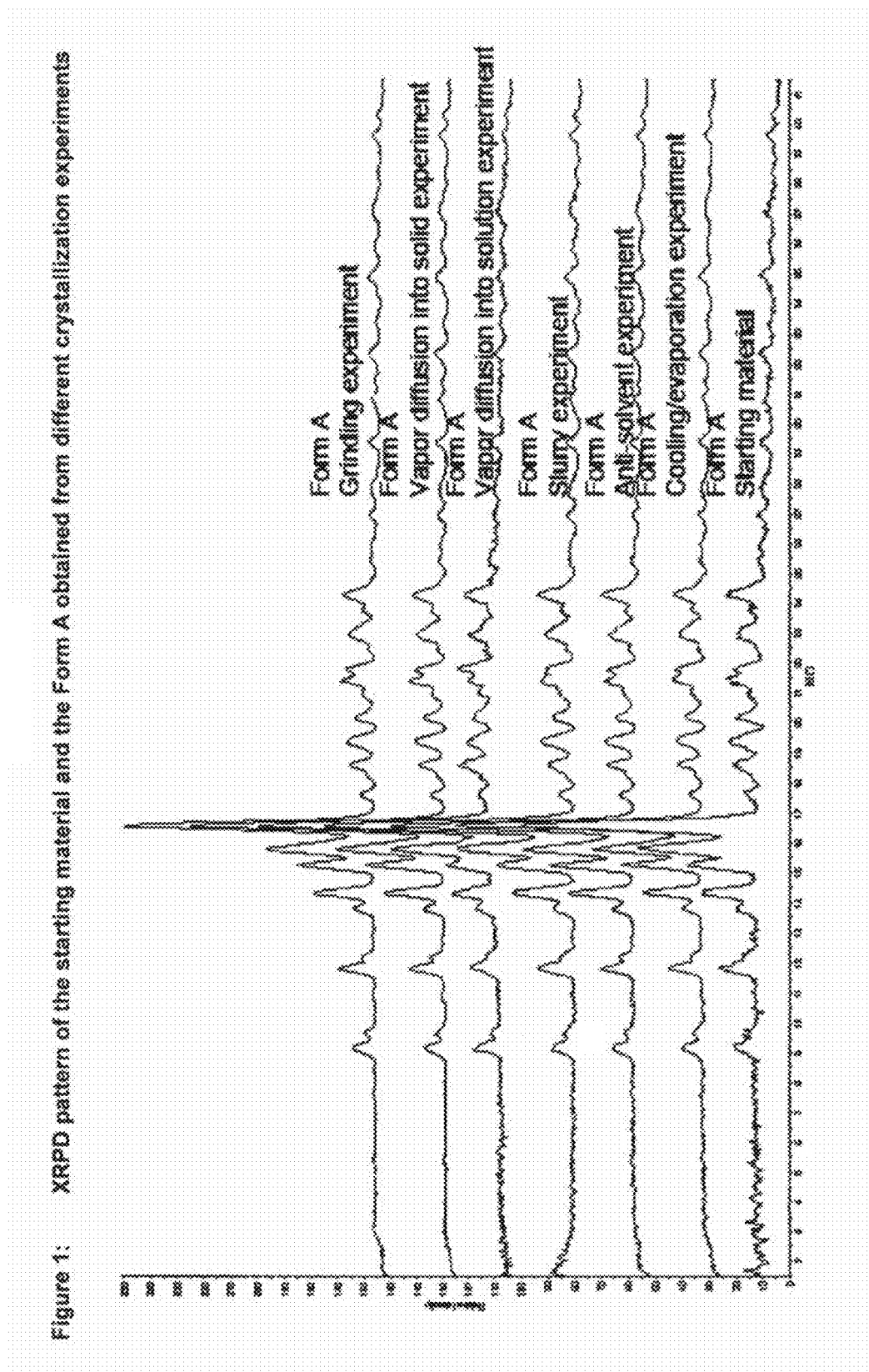
Figure 1: XRPD pattern of the starting material and the Form A obtained from different crystallization experiments Figure 2: Crystal packing and H-bond scheme for Nor-UDCA Form A
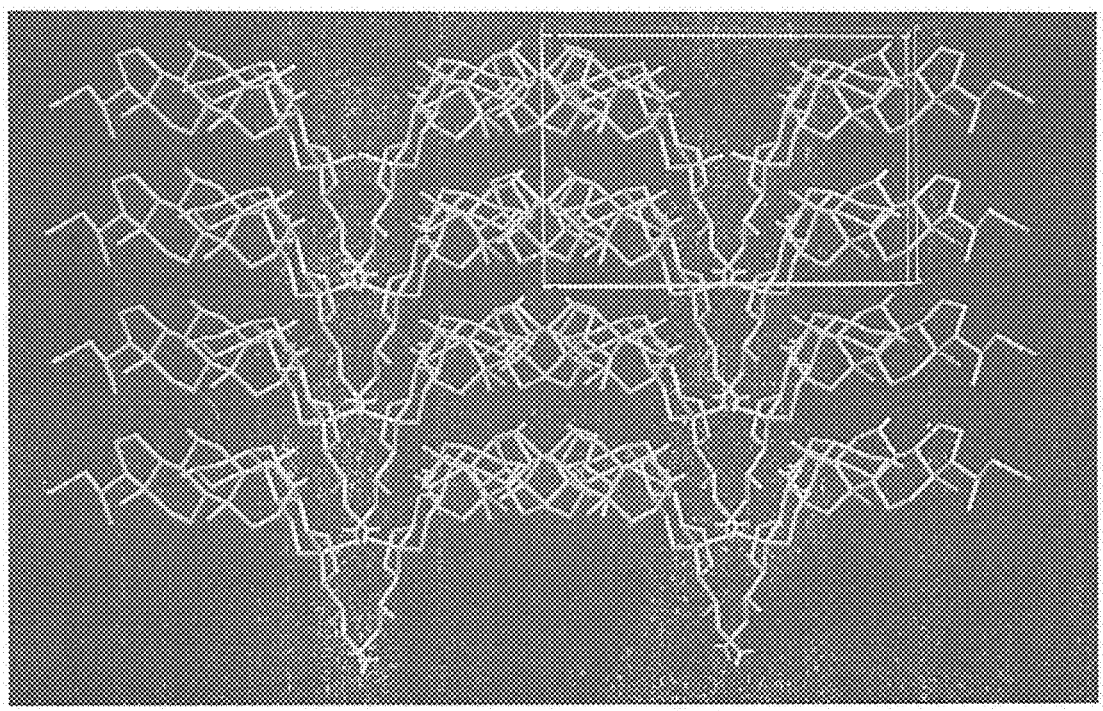

Figure 3: Molecular structure and atom numbering scheme by two symmetrically independent molecules of Nor-UDCA crystals
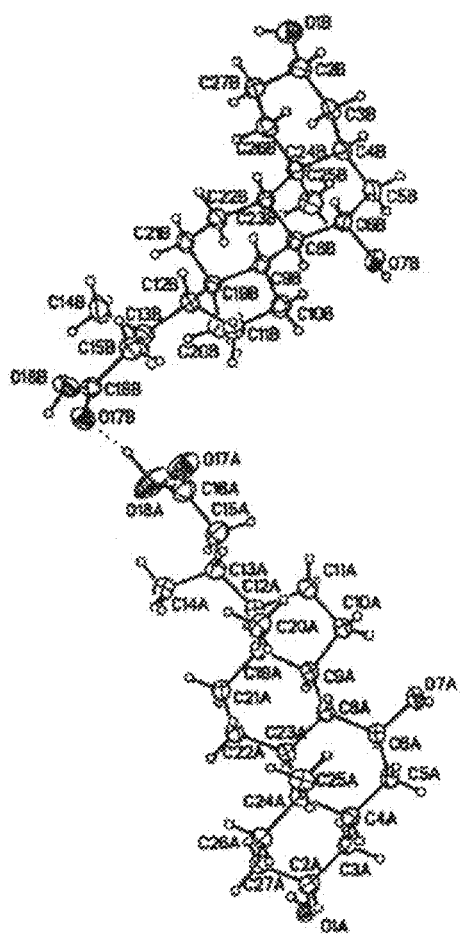

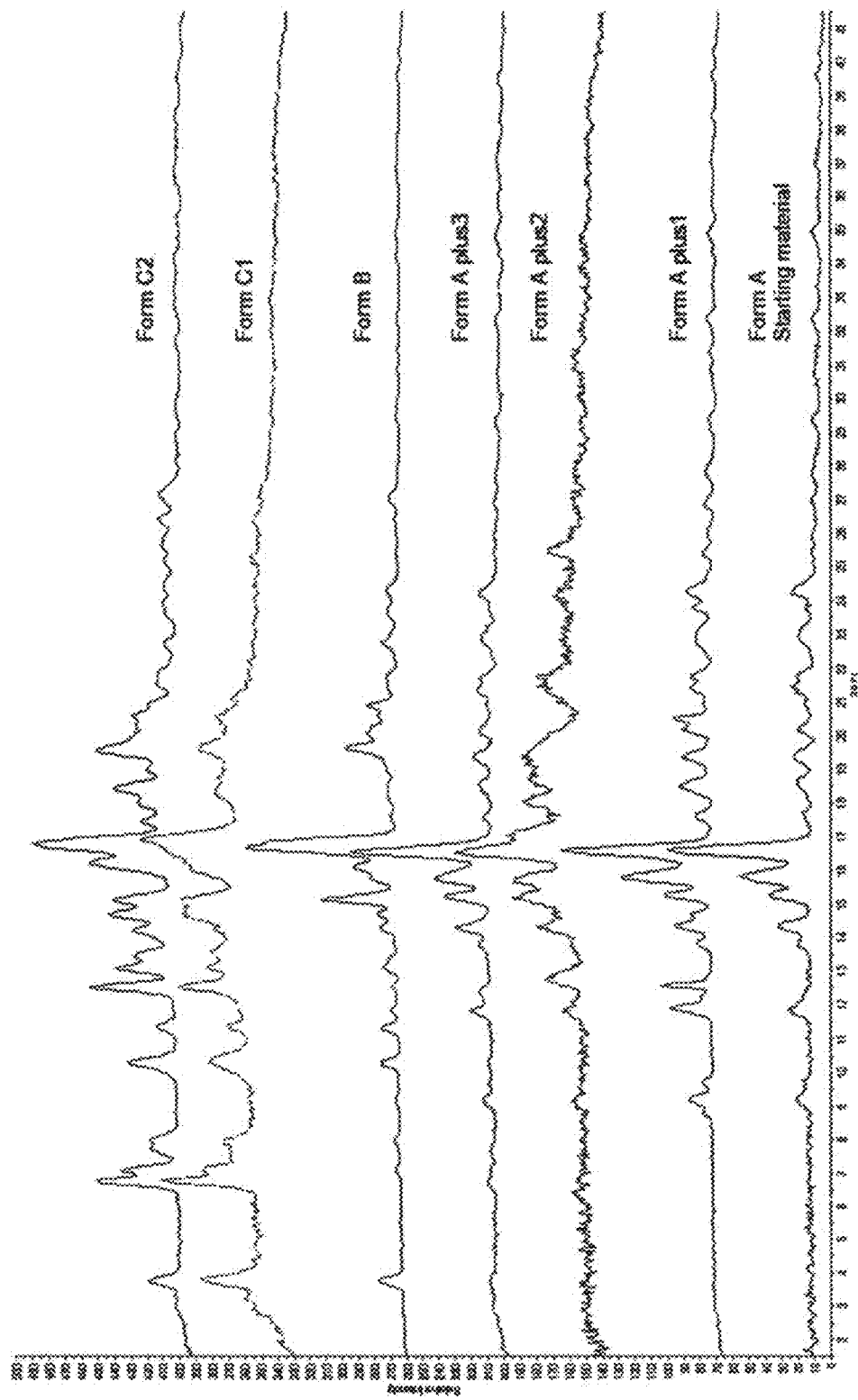

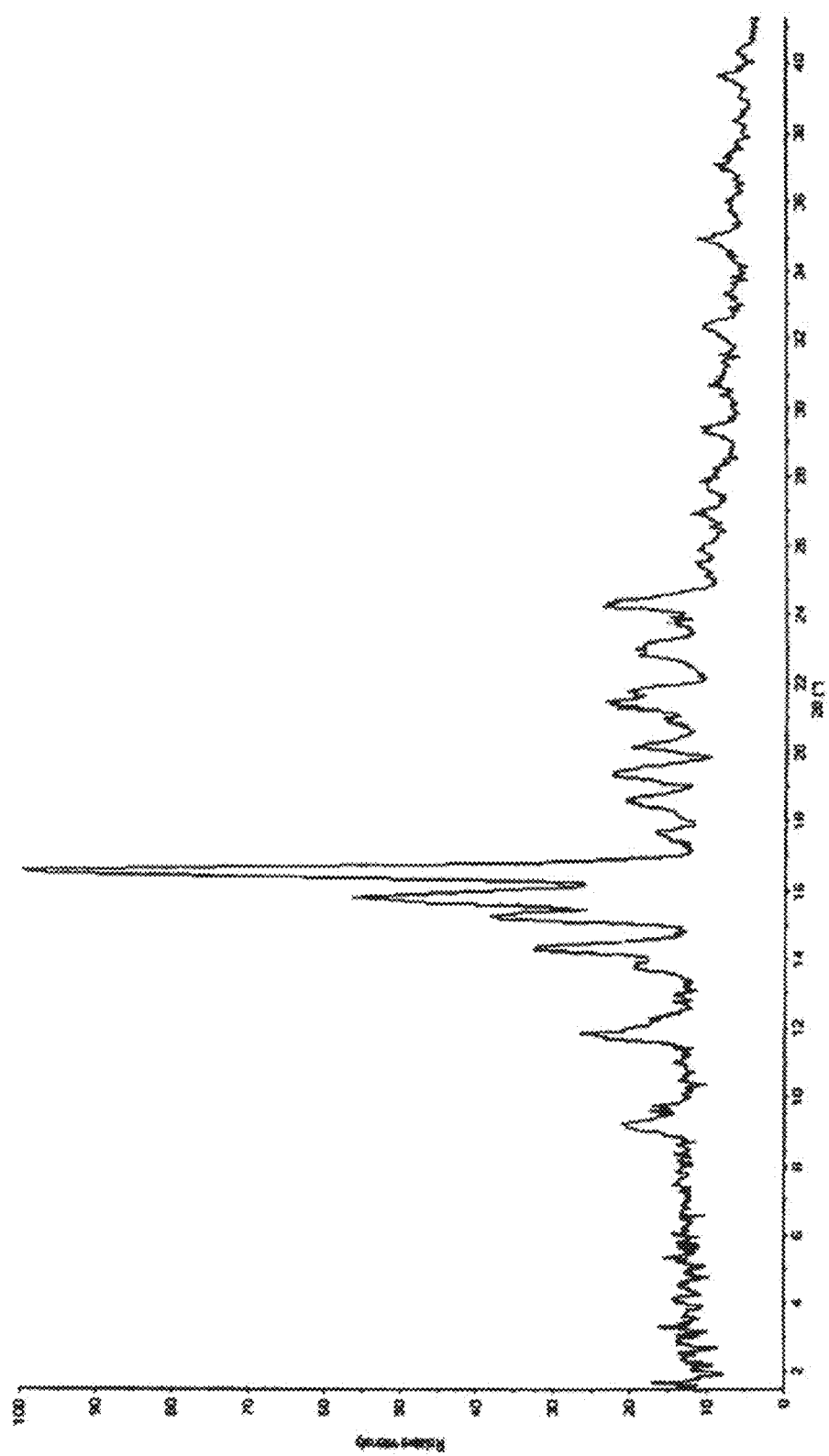

OPTIMIZED SYNTHESIS OF PURE, NON-POLYMORPHIC, CRYSTALLINE BILE ACIDS WITH DEFINED PARTICLE SIZE

CROSS REFERENCE TO RELATED APPLICATIONS

This application is a national stage application of International Application No. PCT/EP2011/071406, filed 30 Nov. 2011, which claims priority from European Patent Application No. 10193143.4, filed 30 Nov. 2010, from which applications priority is claimed, and which are incorporated herein by reference.

The present invention is related to a pharmaceutical, production suited synthesis exceptionally applicable for the treatment of bile- and liver diseases, which contains nor-ursodeoxycholic acid (Nor-UDCA), bis-nor-ursodeoxyeholic acid (Bis-Nor-UDCA) of a pharmaceutical acceptable salt or a derivative thereof.

BACKGROUND OF THE INVENTION

Nor-UDCA and Bis-Nor-UDCA are ursodeoxycholic acid analogs with modified physiochemical properties, like solubility, critically micellar concentration, or hydrophilicity (Roda et al., Dig Dis and Sciences, 1989). A method for the synthesis of 24-nor-5βcholan-23-oic acid was already described by Schteingart and Hofmann (Journal of Lipid Research, 1988). In vitro experiments demonstrated their efficacy in animal models of cholestatic liver disease (PCT/EP2005/052178). A method for the preparation of Nor-UDCA is described in EP 0624595 B1. However, this document is silent with respect to characteristic chemical and physical properties, purity, extent of crystallization and the particle size of the synthesized Nor-UDCA.

The application of bile acids, especially ursodeoxycholic acid, in the treatment of cholestatic liver diseases, like Primary Biliary Cirrhosis, is well known and published already in the eighties of the last century (Poupon et al., Lancet, 1987). While the use of current available pharmaceutical preparations only results in the successful treatment of a subset of patients, there is a need for patients who do not respond the ursodeoxycholic acid therapy or suffer from cholestatic liver diseases or metabolic diseases that are not treatable with ursodeoxycholic acid.

Depending on the pH-value of the solvent bile acids are of low solubility. An adequately good solubility of bile acids in the intestinal tract is a prerequisite for a successful pharmaceutical treatment. Solubility may be improved by salt formation of Nor-UDCA. A second objective is a preparation with a sufficient oral bioavailability. A high in vitro-dissolution rate is a prerequisite for sufficient oral bioavailability. Micronization, e.g. the production of a pharmaceutical preparation with a very small defined particle size (>60% with a diameter of less than 10 μm), is an established method to increase the dissolution rate. A known, but elaborate process to achieve micronized particles is by extensive milling.

An additional objective of the present invention was to provide a physically pure, e.g. crystalline, preparation, which is thermodynamically stable.

The objective of this invention was to synthesize a novel form of Nor-UDCA or Bis-Nor-UDCA at high quality, which has favourable purity, particle size characteristics and that is applicable for the treatment of cholestatic or metabolic liver diseases. The desired crystal form should be obtained in a consistent and reproducible manner by a scalable and industrial production process.

Since crystal modifications of a substance represent different crystal structures with potentially different properties, the main objective of the invention was to identify and select the thermodynamically stable polymorph/single crystalline form of Nor-UDCA that does not convert into another polymorphic form. This particular modification of Nor-UDCA should exhibit considerable chemical and physical advantages over metastable forms and should therefore be the substance of choice for further chemical and pharmaceutical development.

In addition, it is desirable to produce Nor-UDCA with a consistent particle size and morphology because the crystal habit affects important processing parameters such as flowability, bulk density and compressibility. Micronization of Nor-UDCA is preferred to increase the dissolution rate of the compound and by this the oral bioavailability.

The conditions of the purification and crystallisation process should produce the appropriate solid form of Nor-UDCA with reliable and reproducible polymorphic purity, chemical purify, crystal habit and yield. Micronization by milling in order to control the crystal size of Nor-UDCA can be avoided. Thereby, a common phenomenon upon micronization, namely amorphization, can be prevented.

The published method for the synthesis of Nor-UDCA is not suitable to meet pharmaceutical requirements. Especially the purification route is not effective to reach the desired product qualities with regard to polymorphic purify, chemical purity, crystal habit and yield. Conventional methods of purification do not allow to obtain a polymorph of Nor-UDCA or Bis-nor-UDCA having a very high chemical purify, e.g. such that the total amount of impurities is less than 0.05%. In addition, the known methods do not result in a particle size such that the D50 value is less than 10 μm without micronization. In addition, micronization would destroy the polymorphic purity of the product.

SUMMARY OF THE INVENTION

The present invention provides a scaleable and industrial production process that results in a Nor-UDCA preparation or Bis-nor-UDCA preparation with desired quality attributes and pharmaceutical applicability. The inventors surprisingly found that purification and optionally recrystallization of the potassium salt of Nor-UDCA with subsequent precipitation of the free acid provides a novel physically pure and thermodynamically stable crystalline form of Nor-UDCA ("Form A").

In a first aspect, the present invention therefore relates to a pure polymorph of Nor-UDCA or Bis-nor-UDCA, or of a pharmaceutically acceptable salt thereof. The polymorph is thermodynamically stable.

Preferably, the Nor-UDCA, Bis-nor-UDCA, or pharmaceutically acceptable salt thereof is in its anhydrous form. That is, the polymorph crystals contain substantially no water. The amount of water in the crystals is generally less than 1%, preferably less than 0.5%, more preferably less then 0.1%, based on the total weight of the crystal.

The polymorph is characterized by XRPD peaks at 11.9, 14.4, 15.3, 15.8, and 16.6±0.2 degrees of 2-theta. Preferably, the polymorph is characterized by the XRPD pattern as shown in FIG. 4 for "Form A".

A second aspect of this invention is a pharmaceutical composition comprising the polymorph described herein. The pharmaceutical composition preferably exhibits a specific particle size distribution wherein at least 60% of the particles have a size <10 µm.

A third aspect of the invention is the use of the polymorph of the present invention or of the pharmaceutical composition of the present invention, for the treatment of cholestatic liver disease. Preferably, the cholestatic liver disease is selected from the group consisting of primary biliary cirrhosis (PBC), primary sclerosing cholangitis (PSC), autoimmune hepatitis (AIH) and overlap syndromes, including AIH-overlap syndromes.

The polymorph or the pharmaceutical composition described herein may also be used for the treatment of metabolic liver disease. The metabolic liver disease may be non-alcoholic steato-hepatitis or alcoholic steato-hepatitis.

The pharmaceutical composition of the present invention may be formulated for oral, parenteral, subcutaneous, intravenous, intramuscular, nasal, inhalative, topical or rectal administration. It will usually comprise one or more pharmaceutically acceptable excipients.

A fourth aspect of the present invention is a method for the preparation of a pure polymorph of Nor-UDCA or Bis-nor-UDCA, or of a pharmaceutically acceptable salt thereof, comprising the following steps: crystallizing the potassium salt of Nor-UDCA or Bis-nor-UDCA; and optionally dissolving the potassium salt in a solvent and acidifying the solution to obtain pure Nor-UDCA or Bis-nor-UDCA.

The solvent in which the potassium salt is dissolved is preferably a mixture of water and acetone; and the precipitation is carried out by acidifying the solution to have a pH in the range of 1 to 2.

The process described herein leads to the formation of a single solid form of Nor-UDCA (or Bis-nor-UDCA), the crystal structure of which could be refined as monoclinic C2, closed packed without any solvent accessible void. The described process does not show the formation of polymorphic Nor-UDCA or Bis-nor-UDCA. Conversion into other polymorphic forms could also not be observed. The crystalline structure of Nor-UDCA obtained from the synthetic route proves to be the thermodynamically stable form.

Further, the conditions of precipitation of Nor-UDCA from its potassium salt are as such that crystals of a desired particle size can be obtained directly in one step of the production process. An additional milling step to control the particle size of the crystals is therefore not required. This is of great advantage taking into consideration that high-energy operations like grinding and milling (micronization) in general lead to amorphization of Nor-UDCA, thereby to reduced polymorphic purity end chemical purity.

In addition, the yield of Nor-UDCA with pharmaceutical pure quality by this process is at least 45% of the source material and therefore very high compared to published methods.

In summary, it was surprisingly found that the described method of production for Nor-UDCA leads to a single-polymorphic, pure and crystalline substance and does not need micronization, as it is for instance established during the production of UDCA, the preparation currently in use for the treatment of cholestatic liver diseases. The described process is applicable to the preparation of Bis-nor-UDCA accordingly.

The present invention is defined in the claims. The invention further relates to the following aspects (1) to (17):

(1) A pure polymorph of Nor-UDCA or Bis-nor-UDCA, or of a pharmaceutical acceptable salt thereof.

(2) The polymorph of item (1), which is thermodynamically stable.

(3) The polymorph of item (1) or (2), wherein said Nor-UDCA, Bis-nor-UDCA, or pharmaceutically acceptable salt thereof is in its anhydrous form.

(4) The polymorph of any one of items (1) to (3), characterized by XRPD peaks at 11.9, 14.4, 15.3, 15.8, and 16.8±0.2 degrees of 2-theta.

(5) The polymorph of item (4), characterized by the XRPD pattern as shown in FIG. 5.

(6) A pharmaceutical composition comprising the polymorph according to any one of items (1) to (5).

(7) The pharmaceutical composition according to item (6), wherein the particle size distribution in the pharmaceutical composition comprises at least 80% particles with a size <10 µm.

(8) The polymorph according to any one of items (1) to (5), or the pharmaceutical composition according to item (6) or (7), for the treatment of cholestatic liver disease.

(9) The polymorph or the pharmaceutical composition according to item (8), wherein the cholestatic liver disease is selected from the group consisting of primary biliary cirrhosis (PBC), primary sclerosing cholangitis (PSC), autoimmune hepatitis (AIH) and overlap syndromes, including AIH-overlap syndromes.

(10) The polymorph according to any one of items (1) to (5), or the pharmaceutical composition according to item (6) or (7), for the treatment of metabolic liver disease and/or arteriosclerosis.

(11) The polymorph or the pharmaceutical composition according to item (10), wherein the metabolic liver disease is non-alcoholic steato-hepatitis.

(12) The polymorph or the pharmaceutical composition according to item (10), wherein the metabolic liver disease is alcoholic steato-hepatitis.

(13) The pharmaceutical composition according to any one of items (8) to (12), which is formulated for oral, parenteral, subcutaneous, intravenous. Intramuscular, nasal, topical or rectal administration.

(14) The pharmaceutical composition according to any one of items (8) to (13), comprising one or more pharmaceutically acceptable excipients.

(15) A method for the preparation of a pure polymorph of Nor-UDCA or Bis-nor-UDCA, or of a pharmaceutically acceptable salt thereof, comprising the following steps:
  crystallizing the potassium salt of Nor-UDCA or Bis-nor-UDCA; and
  optionally dissolving the potassium salt in a solvent and acidifying the solution to obtain pure Nor-UDCA or Bis-nor-UDCA.

(16) The method of item (15), wherein said solvent is a mixture of water and acetone, and wherein said precipitation is carried out by acidifying the solution to have a pH in the range of 1 to 2.

(17) The method of item (15) or (16), further comprising the following steps:
  converting a compound of formula (A)

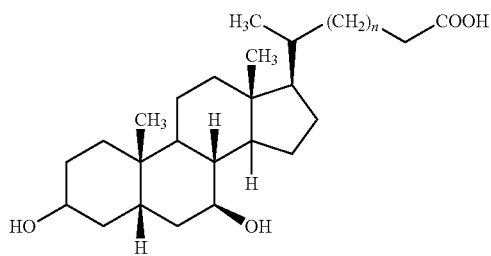

(A)

into a compound of formula (B)

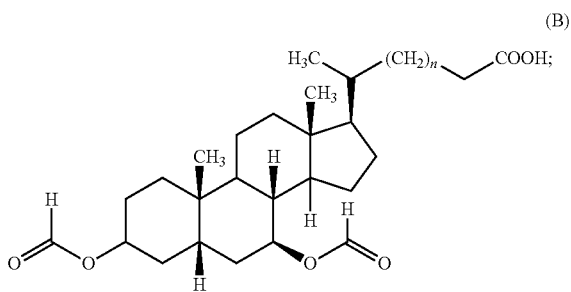

(b) converting the compound of formula (B) into a compound of formula (C)

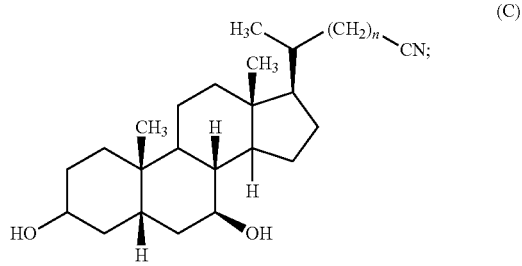

(c) converting the compound of formula (C) into a compound of formula (D) in crude form

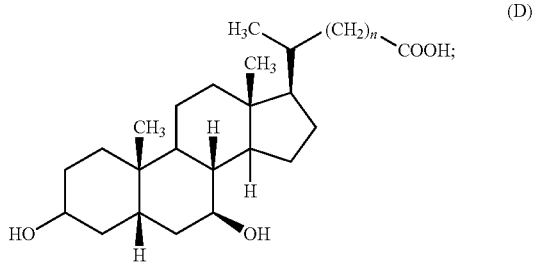

and (d) treating the compound of formula (D) in crude form with KOH under conditions to crystallize the potassium salt of Nor-UDCA or Bis-nor-UDCA;

wherein n is 0 or 1.

BRIEF DESCRIPTION OF DRAWINGS

FIG. 1 is a chart showing the XRPD pattern of the starting material and the Nor-UDCA Form A obtained from different crystallization experiments.

FIG. 2 is a chart showing crystal packing and H-bond scheme for Nor-UDCA Form A.

FIG. 3 is a molecular structure and atom numbering scheme by two symmetrically independent molecules of Nor-UDCA crystals.

FIG. 4 is a chart showing the comparison of XRPD patterns of new forms of Nor-UDCA and XRPD patterns of Nor-UDCA Form A.

FIG. 5 is a chart showing the XRPD pattern of Nor-UDCA Form A.

DETAILED DESCRIPTION OF THE INVENTION

Polymorph

The present invention provides a pure polymorph of Nor-UDCA or Bis-nor-UDCA, or of a pharmaceutically acceptable salt thereof. The polymorph is thermodynamically stable.

Polymorphism is defined as the ability of a substance to crystalline in more than one crystal lattice arrangement. Polymorphism can influence many aspects of solid state properties of a drug. Different crystal modifications of a substance may differ considerably from one another in many respects such as their solubility, dissolution rate and finally bioavailability. An exhaustive treatment of polymorphism in pharmaceutical and molecular crystals is given e.g. by Byrn (Byrn, S. R., Pfeiffer, R. R., Stowell, J. G., "Solid-State Chemistry of Drugs", SSCI Inc., West Lafayette, Ind., 1999), Brittain, H. G., "Polymorphism in Pharmaceutical Solids", Marcel Dekker, Inc., New York, Basel, 1999) or Bernstein (Bernstein, J., "Polymorphism in Molecular Crystals", Oxford University Press, 2002).

The term crystalline refers to any non-amorphous form of the active pharmaceutical ingredient (API). The term "amorphous form" refers to a form of the API which has no long-range order like crystalline structures. The atoms or molecules of a material present in amorphous form are arranged in a non-uniform array. It is for example possible to distinguish amorphous from crystalline forms of a compound by powder X-ray diffraction.

The term "crystalline polymorph" or "polymorph" as described herein, refers to a specific crystal form of an active pharmaceutical ingredient which can be characterized by analytical methods such as e.g. X-ray powder diffraction or IR-spectroscopy.

Preferably, the Nor-UDCA, Bis-nor-UDCA, or pharmaceutically acceptable salt thereof is in its anhydrous form. That is, the polymorph crystals contain substantially no water. The amount of water in the crystals is generally less than 1%, preferably less than 0.5%, more preferably less than 0.1%, based on the total weight of the crystal.

A polymorph is "pure" in the sense of the present invention if it is suitable for pharmaceutical application and contains less than 2% impurities. The amount of impurities in the polymorph of the present invention is generally less than 2%. preferably less than 1%, more preferably less than 0.5%, more preferably less than 0.1% based on the total weight of the preparation. The amount of any single impurity in the polymorph of the present invention is preferably less than 0.1%, more preferably less than 0.05%, most preferably less than 0.03% based on the total weight of the preparation. In a first embodiment, the total amount of impurities in the polymorph of Nor-UDCA is less than 2%, preferably less than 1%, more preferably less than 0.5%, more preferably less than 0.1% based on the total weight of the Nor-UDCA. The amount of any single impurity in the polymorph of Nor-UDCA is preferably less than 0.1%, more preferably less than 0.05%, most preferably less than 0.03% based on the total weight of the Nor-UDCA. In a second embodiment, the total amount of impurities in the polymorph of Bis-nor-UDCA is less than 2%, preferably less than 1%, more preferably less than 0.5%. more preferably less than 0.1% based on the total weight of the Bis-nor-UDCA. The amount of any single impurity in the polymorph of Bis-nor-UDCA is preferably less than 0.1%, more preferably less than 0.05%, most preferably less than 0.03% based on the total weight of the Bis-nor-UDCA.

Impurities can be determined as described herein in Example 2, The impurity profile of Nor-UDCA is specified by known and unknown impurities. Known impurities are Ursodeoxycholic acid (UDCA) and 3α,7β-dihydroxy-24-nor-5β-cholane-23-amide (Amide). UDCA, also referred to as impurity A, is the starting material of the synthesis of Nor-UDCA while the Amide, also referred to as impurity B, represents an intermediate formed in step 3 of the synthesis of Nor-UDCA. Unknown impurities might result from the synthetic route hut also from the degradation of Nor-UDCA.

The polymorph of the present invention is preferably single-polymorphic, i.e. it essentially consists of a single polymorph, and/or it has polymorphic purity. The amount of amorphous Nor-UDCA (or Bis-nor-UDCA, respectively) in the polymorph of the present invention is typically negligible. Preferably, no amorphous Nor-UDCA or Bis-nor-UDCA in the polymorph of the present invention is detectable, e.g. by XRPD. More preferably, the polymorph of the invention contains substantially no amorphous Nor-UDCA (or Bis-nor-UDCA, respectively). Most preferably the polymorph of the invention does not contain any amorphous Nor-UDCA (or Bis-nor-UDCA, respectively). The amount of the polymorph of Form A in the polymorph of the present invention is preferably at least 90%, more preferably at least 90.5%, more preferably at least 99.9%, most preferably substantially 100%, based on the total weight of the Nor-UDCA (or Bis-nor-UDCA, respectively).

The polymorph of the invention is thermodynamically stable. The polymorph of the invention was found with high occurrence in all types of crystallisation modes and also formed from different pure solvents and mixtures. Even in the crystallization experiments starting with amorphous form of NorUDCA produced by grinding (for vapour diffusion onto solids) or by evaporation of freeze-dried solution (cooling/evaporation experiments) to erase memory effects of Form A, the XRPD analyses performed on the isolated solids showed that predominantly Form A was obtained. Surprisingly, the invention allows to grow single crystals of Form A.

The particle size distribution of the polymorph of the invention is preferably such that at least 60% of the crystals have a particle size of less than 10 μm.

The polymorph of the present invention preferably has a D50 of less than 10 μm. For example, the D50 may range from 0.5 μm to 10 μm, more preferably from 1 μm to 9 μm, more preferably from 2 μm to 8 μm, most preferably from 3 μm to 7 μm. The polymorph of the present invention preferably has a D90 of less than 30 μm. For example, the D90 may range from 2 μm to 30 μm, more preferably from 5 μm to 25 μm, more preferably from 8 μm to 20 μm, most preferably from 10 μm to 18 μm. The polymorph of the present invention preferably has a D95 of less than 30 μm. For example, the D95 may range from 3 μm to 30 μm, more preferably from 6 μm to 28 μm, more preferably from 9 μm to 25 μm, most preferably from 10 μm to 20 μm.

D50, D90 and D95 represent the median or the 50th percentile, the $90^{th}$ percentile and the 85th percentile of the particle size distributions respectively, as measured by volume. That is, D50 (D90; D95) is a value on the distribution such that 50% (90%; 85%) of the particles have a volume of this value or less.

The particle size distribution can be determined as described herein in Example 3 and/or according the European Pharmacopeia (Ph. Eur.), edition 6.8. section 2.9.31, preferably with a Mastersizer 2000 by Malvern instruments. The evaluation is typically carried out by the Fraunhofer model.

Method for Preparing the Polymorph

The method for preparing the polymorph of the invention preferably comprises the following steps:

(a) converting a compound of formula (A)

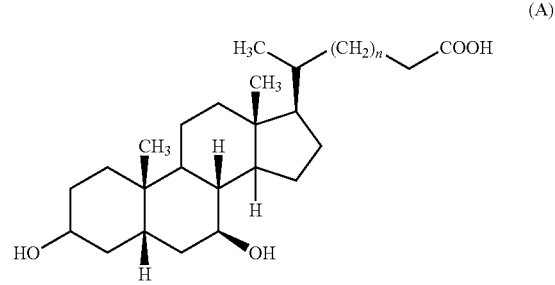

into a compound of formula (B)

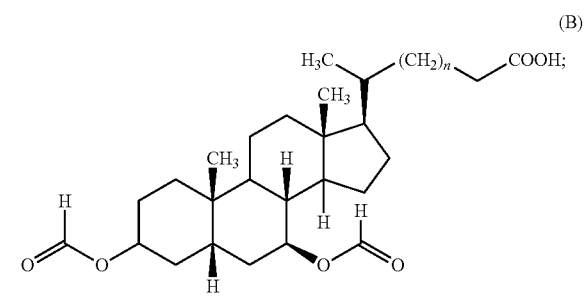

(b) converting the compound of formula (B) into a compound of formula (C)

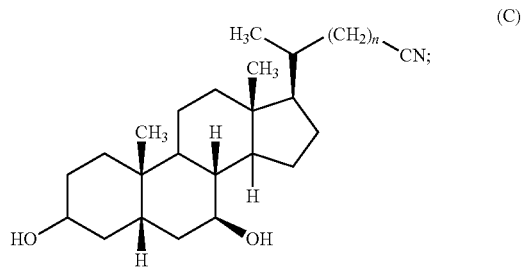

(c) converting the compound of formula (C) into a compound of formula (D) in crude form

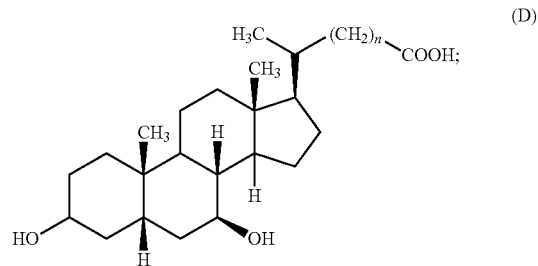

and (d) treating the compound of formula (D) in crude form with KOH under conditions to crystallize the potassium salt of Nor-UDCA or Bis-nor-UDCA:

wherein n is 0 or 1.

The potassium salt obtained in step (d) can be converted into the pure form of compound (D) by dissolving the potassium salt in a solvent, acidifying the solution so as to obtain crystals of pure compound (D).

When n=1, the starting compound of formula (A) is UDCA, and the product of formula (D) is Nor-UDCA.

When n=0, the starting compound of formula (A) is Nor-UDCA, and the product of formula (D) is Bis-nor-UDCA.

The solvent is preferably a mixture of 2-propanol and water, wherein the 2-propanol may be added first, followed by the water until the potassium salt has dissolved completely.

In the following, preferred embodiments of the method of the invention, highlighting advantages thereof, are described. Each of the following steps, and each of the substeps thereof, can be combined with other embodiments of this invention. In particular, any of the features of the following embodiments can be combined with the embodiments described above.

Step 1: Preparation of
3α,7β-diformyloxy-5β-cholan-24 oic acid (I)

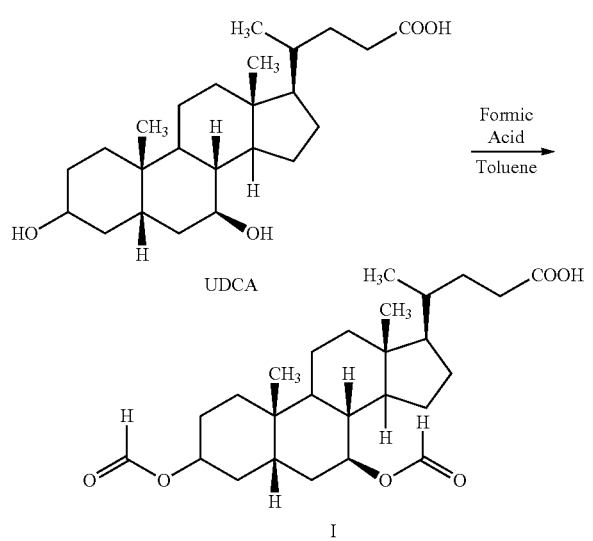

a) Process Description (Protection)

UDCA is added to formic acid and toluene (>3 hours at 65 to 75° C.; reducing the temperature to 18 to 22° C.). The toluene phase is separated and the formic acid/water phase is discharged. The toluene phase is concentrated (≤65° C.) and n-heptane is added quickly at 55 to 65° C. to crystallize the product. The reaction mixture is cooled to 10 to 15° C. and stirred. The suspension is filtered, washed with n-heptane and dried at maximum 50° C. (LCD: ≤1.0%), Product I is obtained as a white solid.

b) Differences Compared to the Published Synthesis

Perchloric acid was left out to simplify the process and addition of acetic acid anhydride was left out to avoid the powerful gas evolving. To obtain a more pore product and a better crystallization process, the reaction mixture is in situ extracted into toluene and the product was crystallized from toluene/n-heptane. Moreover, commercial aqueous formic acid could be employed and the need for anhydrous reaction conditions could be avoided. The precipitation from toluene/heptane furthermore serves as a method of further purifying the product. This step results in addition in an enhanced yield of approximately 85%.

Step 2: Preparation of 3α,7β-dihydroxy-24-nor-5β-cholan-23-nitrile (II)

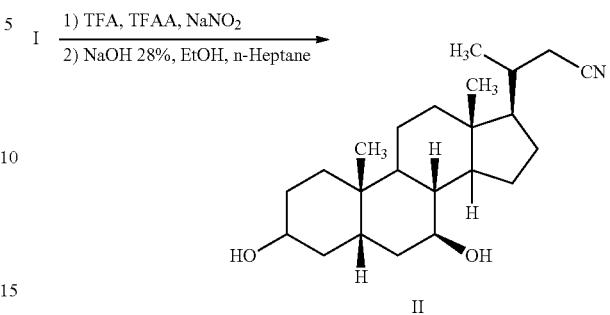

a) Process Description (Re-Arrangement)

Trifluoroacetic acid, product I, and trifluoracetic acid anhydride are mixed (>40 min at 15 to 25° C.). The reaction mixture is stirred and cooled, while sodium nitrite is added (1.5 to 3 hours at 15 to 25° C.). The reaction mixture is very gently heated to 35 to 40° C. and the temperature is kept constant for ≥45 min. Then, the temperature is raised to 44 to 48° C. and kept constant for 30 min. After cooling to <22° C. toluene and water are added. The phases are separated and the water/acid phase is discharged. Water is added to the toluene phase and discharged after separation. Toluene is distilled off at <50° C. to give a highly viscous oil. EtOH, n-heptane and NaOH 28% are added to the oil, heated to 55-65° C. for 1.5 hrs, and product II starts to crystallize. Water is added and the suspension is cooled to 16 to 22° C. The suspension is filtered, the cake is washed with EtOH/water followed by n-heptane and dried <50° C. (LOD: ≤1.0%). Product II is obtained as a white to light yellow solid.

b) Differences Compared to the Published Synthesis

The volume of trifluoroacetic acid was reduced to minimize the use of harmful and expensive chemicals. To optimize safety and purity, temperature intervals and time intervals during addition of sodium nitrite and heating were modified. The work-up procedure was modified in order to be practical in production scale and to increase the purity. The reaction mixture was extracted with toluene and was afterwards fully deprotected with sodium hydroxide in EtOH/water/n-heptane. The product was crystallized from alkaline EtOH/water/n-heptane. This is in contrast to the published method by Schteingart (1988), a method without crystallization of the product and thus no element of purification.

Yields obtained by the revised process are around 80%.

Step 3: Preparation of
3α,7β-dihydroxy-24-nor-5β-cholan-23oic acid (III)

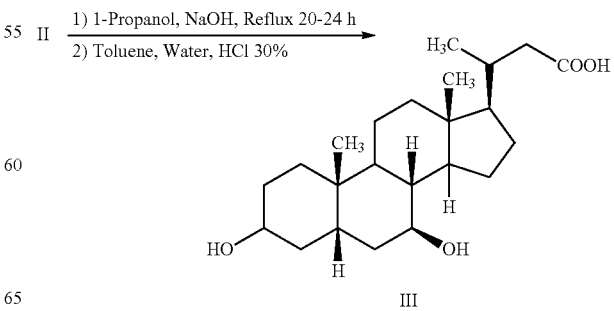

a) Process Description (Hydrolysis)

Product II, n-propanol and sodium hydroxide (pellets) are mixed in a steel reactor. The reaction mixture is stirred and refluxed until hydrolysis is complete (>20 h). Water is added and n-propanol/water are distilled off, keeping the temperature above 45° C. Toluene-Water is added, while the reaction mixture is stirred efficiently and the temperature is kept at 65 to 65° C. The pH is adjusted to 1.0 to 2.0 with HCl 30%. Product III (crude nor-UDCA including impurities at a yield of app. 95% by UV detection at 290 nm) crystallizes from the two-phase system during the pH adjustment. The suspension is cooled to 18 to 22° C. The suspension is filtered and the filter cake is washed with water and n-heptane and dried at maximum 50° C. (LOD: ≤1.0%).

b) Differences Compared to the Published Synthesis

The reaction time was significantly reduced by changing the solvent from EtOH:water 1:1 to pure n-propanol and by changing from potassium hydroxide to sodium hydroxide. The volume of solvent was also reduced. Washing and extraction were left out in the work-up procedure and instead the product was crystallized directly from a two-phase system of water and toluene. This method is much more simplified: it safes time, reduces toxic solvents, uses non-toxic materials and thus crystallisation is subject to improved control. Crystallisation from this two-phase system provided an excellent product quality With a yield of at least 90%.

Step 4: Preparation of 3α,7β-dihydroxy-24-nor-5β-cholan-23-oic acid potassium salt (Nor-UDCA potassium salt, IV)

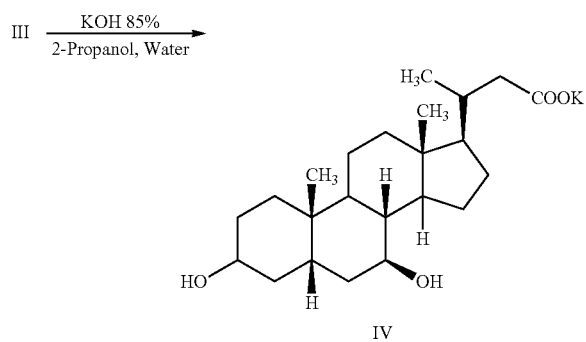

a) Process Description (Purification)

Product III, 2-propanol and one equivalent of potassium hydroxide are mixed and heated to 70 to 80° C. Water is slowly added until a solution is obtained. The solution is light yellow to yellow and slightly turbid. Active carbon and perlite are added and the solution is filtered while hot. Under reduced pressure 2-propanol/water are distilled off at 40 to 80° C. By addition of 2-propanolol, the distillation is continued until the water content is ≤2%. Thereafter, the suspension is cooled to 5 to 15° C. (≥4 hours). The temperature is towered to 0 to 5° C. and product IV is filtered off, washed with 2-propanol and dried under reduced pressure ≤50° C. Product IV is obtained as a white solid. In case the obtained potassium salt is not of sufficient purity it can be re-crystalised: Product IV and 2-propanol are mixed and heated to 75 to 80° C. Water is added until a solution is obtained, 2-Propanol/water are distilled off under reduced pressure at 40 to 80° C. During the distillation product IV starts crystallizing. Again, the distillation is continued until the water content is ≤2%. 2-Propanol is added and the suspension is cooled to 5 to 15° C. (≥4 hours). The temperature is lowered to 0 to 5° C. and product V is filtered off, washed with 2-propanol and dried under reduced pressure ≤50° C. The re-crystallization is repeated until the test for purity is compliant (product V is obtained pharmaceutical pure and at very high yields of ≥98%, a proof of very efficient purification).

b) Differences Compared to the Published Synthesis

A new purification step of the synthesis is described, not published in the state of the art.

Step 5: Preparation of Nor-UDCA Pure (VI)

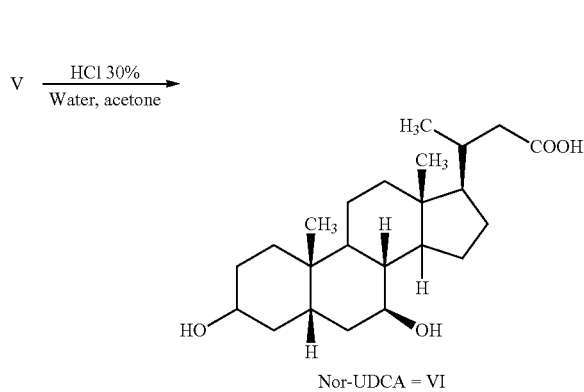

a) Process Description (Final Precipitation)

Product V, water and acetone are stirred at 22 to 28° C. to obtain a solution. The solution is filtered. The pH of the reaction mixture is adjusted to 1.0 to 2.0 with slow addition of HCl 30%. Product VI immediately starts crystallizing. The suspension is cooled to 18 to 24° C., filtered off, washed with water for injections, water for injections/acetone, and n-heptane and dried under reduced pressure at ≤50° C. (LOD: ≤0.8%). The yield is at least 90%.

b) Differences Compared to the Published Synthesis

In the published procedure Nor-UDCA is purified by ion exchange column chromatography and re-crystallization from methanol/acetone. The most effective purification method was identified to be the formation and/or alternatively recrystallization of Nor-UDCA potassium salt from 2-propanol/water followed by precipitation of the free acid from water/acetone. This purification method proved to be very effective in removing both the known impurity A (amide) and B (UDCA) as well as unknown impurities. Finally, after sieving nor-UDCA is synthesized at high quality with a defined particle size distribution (60%<10 μm) as required for pharmaceutical applications.

Pharmaceutical Compositions

The invention also relates to a pharmaceutical composition comprising the polymorph of the invention.

The pharmaceutical composition may comprise one or more suitable excipients which are pharmaceutically acceptable.

According to a special embodiment of the present invention the polymorph can be formulated for oral or intravenous administration, wherein these formulations further comprise pharmaceutically acceptable carriers, adjuvants, excipients and/or vehicles.

Solid dosage forms for oral administration can include tablets, preferably effervescent or chewable tablets, capsules, pills, powders and granules. In such solid dosage forms, the polymorph can be admixed with regularly used substances like sucrose, mannitol, sorbitol, starch and starch derivatives, cellulose and cellulose derivates (e.g. microcrystalline cellulose), di-calcium phosphate, lactose, colloidal anhydrous silica, talc, lubricating agents (e.g. magnesium stearate, macrogols), disintegrants and buffering agents. Tablets and pills can also be prepared with enteric coatings in order to prevent that API is affected by the stomach acids and enzymes.

Liquid dosage forms for oral administration can include pharmaceutically acceptable emulsions, solutions, suspensions and syrups containing inert diluents commonly used in the art, such as water or ethanol/water mixtures. These dosage forms may contain microcrystalline cellulose, alginic acid or sodium alginate, methylcellulose and alike to adjust rheological properties, sweeteners/flavouring agents, and/or employing sorbic acid or other suitable antimicrobial preservatives. When administered by nasal aerosol or inhalation, the compositions according to the present invention may be prepared as solutions in saline, employing benzyl alcohol or other suitable preservatives, absorption promoters to enhance bioavailability, fluorocarbons and/or other solubilizing or dispersing agents.

Suppositories for rectal administration of the API can be prepared by mixing the polymorph with a suitable non-irritating excipient such as hard fat, cocoa butter and polyethylene glycols which are solid at room temperature but liquid at rectal temperature, such that they will melt in the rectum and release the API and optionally other active compounds present in said suppositories.

Injectable preparations, for example sterile injectable aqueous or oleaginous suspensions, can be formulated according to the known art using suitable dispersing agents, wetting agents and/or suspending agents. The sterile injectable preparation can also be a sterile injectable solution or suspension in a nontoxic parenterally acceptable diluent or solvent. Among the acceptable vehicles and solvents that can be used are water and isotonic sodium chloride solution. Sterile fixed oils are else conventionally used as a solvent or suspending medium.

The dosage forms comprising the polymorph of the invention can further include conventional excipients, preferably pharmaceutically acceptable organic or inorganic carrier substances which do not react with the active compound. Suitable pharmaceutically acceptable carriers include, for instance, water, salt solutions, alcohol, oils, preferably vegetable oils, polyethylene glycols, gelatin, lactose, amylose, magnesium stearate, surfactants, perfume oil, fatty acid mono-glycerides and diglycerides, petroethral fatty acid esters, hy-droxymethyl-cellulose, polyvinylpyrrolidone and the like. The pharmaceutical preparations can be sterilized and if desired, mixed with auxiliary agents, like lubricants, preservatives, stabilizers, wetting agents, emulsifiers, salts for influencing osmotic pressure, buffers, colorings, flavoring and/or aromatic substances and the like which do not deleteriously react with the active compounds. For parenteral application, particularly suitable vehicles consist of solutions, preferably oily or aqueous solutions, as well as suspensions, emulsions, or implants.

Various delivery systems are known and can be used to administer the API, including, for example, encapsulation in liposomes, emulsions, microparticles, microcapsules and microgranules (see, e.g., EP 1 317 925). The required dosage can be administered as a single unit or in a sustained release form. The required dosage form may further be administered in a multiple unit form, in immediate, sustained, prolonged, or extended release form, prepared by coating, as a matrix formulation and the like.

The bioavailability of the API may be enhanced by micronization of the formulations using conventional techniques such as grinding, milling end spray drying in the presence of suitable excipients or agents such as phospholipids or surfactants. However, in a special embodiment no grinding and milling is required as the polymorph of the invention already has a suitable particle size.

The API may be formulated in a pharmaceutically acceptable salt form. Pharmaceutically acceptable salts of the API include preferably metal salts, in particular alkali metal salts, or other pharmaceutically acceptable salts. Pharmaceutically acceptable base addition salts include metallic salts made from lithium, aluminum, calcium, magnesium, potassium, sodium and zinc or organic salts made from primary, secondary and tertiary amines and cyclic amines.

The pharmaceutical composition comprises preferably an effective amount of Nor-UDCA or Bis-nor-UDCA and a pharmaceutically acceptable carrier and/or excipient.

According to a preferred embodiment of the present invention the pharmaceutical composition comprises 10 to 8000 mg, preferably 25 to 5000 mg. more preferably 50 to 1500 mg, in particular 250-500 mg, of Nor-UDCA or Bis-nor-UDCA.

On average the Nor-UDCA, Bis-nor-UDCA and/or pharmaceutical acceptable salts thereof may preferably be administered to a patient in an amount of 25 mg to 5 g, preferably 100 mg to 2.5 g, in particular 80.0 mg to 1.5 g per day. However, 1 g of Nor-UDCA, Bis-nor-UDCA and/or pharmaceutical acceptable salts and esters thereof is most preferably administered to a patient. It is further noted that Nor-UDCA, Bis-nor-UDCA and/or pharmaceutical acceptable salts thereof may be administered to an individual in 1-3000 mg/d, preferably 10-2000 mg/d, more preferably 100-1500 mg/d, e.g., 100, 200, 300, 400, 500, 600, 700, 750, 800, 900, 1000, 1100, 1200, 1300, 1400 or 1600 mg/d, in particular 500 or 750 or 1000 or 1500 mg/d. Said amounts are administered preferably at once or possibly in more than one dose (at least 2, 3, 4, 5 or 10 doses) per day. The drug or the pharmaceutical composition according to the present invention may be administered for more than one week, preferably more than four weeks, more preferably more than six months, most preferably more than one year, in particular lifelong.

Nor-UDCA, Bis-nor-UDCA or salts thereof can be administered not only in combination with pharmaceutically acceptable carriers and in dosage forms as described herein, but, of course, also in combination with one or more additional active ingredients (e.g. ursodeoxycholic acid, NSAID, like sulindac and ibuprofen) which are also known to be effective against the same or a similar disease to be treated (e.g. ursodeoxycholic acid) or against another disease, which may be preferably a result of a liver disease.

Pharmaceutical Use of the Polymorph

The liver disease to be treated according to the present invention may be a cholestatic liver disease, preferably primary sclerosing cholangitis (PSC), primary biliary cirrhosis (PBC) or progressive familial intrahepatic cholestasis, in particular progressive familial intrahepatic cholestasis type 1, 2 and 3, cystic fibrosis, drug-induced cholestasis or a noncholestatic liver disease such as chronic viral hepatitis (B, C, D), alcoholic and non-alcoholic steatohepatitis, autoimmune hepatitis, hemochromatosis, Wilson disease and alpha-1-antitrypsin deficiency.

The API of the invention may be used alone or in combination with other anti-inflammatory drugs, like NSAIDs (e.g. ibuprofen, sulindac) and/or in combination with ursodeoxycholic acid or 5-aminosalicylic acid.

According to another preferred embodiment of the present invention the liver disease is primary sclerosing cholangitis (PSC) and/or primary biliary cirrhosis (PBC).

According to another preferred embodiment of the present invention the disease to be treated is a metabolic disease, e.g. non-alcoholic-steato-hepatitis, diabetes, and/or hyperlipidemia. According to yet another preferred embodiment of the present invention the disease to be treated is arteriosclerosis.

EXAMPLES

Reference Example

Various properties of Nor-UDCA synthesized according to Schteingart and Hofmann (1988) Journal of Lipid Research Vol. 29(10), 1387-1385 were investigated.

Chemical Purity

The chemical impurity profile of the synthesized Nor-UDCA was evaluated by HPLC/RI. The following results were obtained:

| | |
|---|---|
| Impurity A | 0.15% |
| Impurity B | ≤0.03% |
| | (reporting threshold) |
| Unknown impurity 1 (RRT = 8.53) | 0.51% |
| Unknown impurity 2 (RRT = 0.84) | 0.09% |
| Total | 0.75% |

The total amount of impurities should be less than 0.05% if the compound is to be used for pharmaceutical purposes. The Nor-UDCA synthesized according to Schteingart and Hofmann failed to meet this requirement. It was tried to further purify the compound by repeated re-crystallizations. However, it was not possible to reduce the total amount of impurities to less than 0.05%.

Particle Size Distribution

The particle size of the crystals obtained was analyzed by microscopy. The median particle size was found to be 13.37 μm, i.e. 50% of the crystals had a size of 13.37 μm or less. 60% of the crystals had a particle size of 15.64 μm or less. 95% of the particles had a particle size of 46.64 μm or less. Less than 30% of the particles had a particle size of 10 μm or less. This particle size distribution is not suitable for the intended pharmaceutical preparation. Milling/micronization is not desired as this would result in a reduction of the polymorphic purity and/or of the thermodynamic stability of the Nor-UDCA.

Example 1

Polymorphic Purity of the Synthesized Nor-UDCA

The polymorph screening study was carried out in two phases. In Phase 1, the synthesized Nor-UDCA, designated Form A, was characterised by XRPD, digital imaging, thermal analysis (DSC and TGMS). The purity of the material was checked by HPLC/RI. A summary of the analytical methods is provided in Table 1. A qualitative solubility determination with 20 solvents was carried out in order to fit the data for the selection of the crystallization solvents to be employed in the polymorph screen. Additionally, the solids recovered by evaporation of solutions used in the solubility experiments were analyzed by XRPD and digital imaging to obtain information on the potential form formation of new forms of Nor-UDCA (see Table 2). Grinding tests were conducted in order to support the definition of the experimental space for this crystallization mode. Amorphous material to be used as starting material was intentionally produced by freeze-drying from 1,4-dioxane/water (95/5%) solution and by grinding (ball-milling) for "cooling/evaporation and vapour diffusion into solids experiments". In Phase 2, 217 experiments divided across different crystallization modes were performed. The applied crystallization modes were:

Combined cooling/evaporative crystallization experiments starting with amorphous material
Crystallization with forward anti-solvent addition
Slurry experiments at two temperatures
Vapour diffusion into solutions
Vapour diffusion onto amorphous solids
Crystallization by grinding with 24 solvents and one dry.

Upon completion of the experiments, XRPD and digital images analyses were performed on all crystallized solids. Following the identification of stable forms, the assessment of their nature and relative stability versus the starting material form was proved by thermal analyses and XRPD re-analyses after storage.

The results of the polymorph screen of Nor-UDCA showed that Form A was found with high occurrence in all types of crystallization modes and also formed from different pure solvents end mixtures (see FIG. 1), Even in the crystallization experiments starting with the amorphous form of Nor-UDCA produced by grinding or by evaporation of freeze-dried solution to erase memory effects of Form A, the XRPD analyses performed on the isolated solids showed that mainly Form A was obtained. It appears to be easy to grow single crystals of Form A, as single crystals were observed to have grown in the vapour diffusion into solution experiments. That suggests that gradually increasing the supersaturation by the slow diffusion time of anti-solvent plays a role in allowing the crystal growth of Form A. The generally observed crystal habit was bulky-like. The crystal structure of Nor-UDCA was determined from single-crystal X-ray diffraction data collected at 294K and crystallized in the monoclinic system with C2 space group (Z'=2) (see Table 3). The crystal structure of Nor-UDCA was successfully refined with a GOF of 1.002 (see Table 3). The crystal packing and H-bonding scheme of Nor-UDCA is presented in FIG. 2. Nor-UDCA presented only intramolecular H-bonds forming monomers repeating periodically. H-bonds are formed between different hydroxyl groups, Nor-UDCA molecules are closed packed following a zigzag pattern and without any solvent accessible void (see FIG. 3).

Three additional unstable forms (Form B, Form C1 and Form C2) were identified in cooling/evaporation experiments. Form C1 was also obtained from an anti-solvent followed by a combined cooling/evaporation experiment. The XRPD's of the three forms are similar, even highly similar in the case of Forms C1 and C2, which indicates the possibility of being isomorphic types of structures. Form C1 was sufficiently stable to allow for determination of its solvated nature. Due to their instability, the nature of Form B and Form C2 could not be determined. Having the similarities of the XRPD patterns as well as the similarities of the molecular structure of the crystallization solvents from which the forms were crystallized out, one may think that Forms B and C2 are solvated structures as well.

Three additional unstable mixtures (Form A plus1, Form A plus2 and Form A plus3) were identified. The mixture Form A plus1 is a mixture of Form A with another possible form obtained from cooling/evaporation experiments. The mixture Form A plus2 is a mixture of Form A with another possible form obtained from slurry experiments at low temperature. The mixture Form A plus3 is a mixture of Form A with another possible form obtained after de-solvation or transformation of Form C1 (obtained from cooling/evaporation experiments) during storage at ambient conditions. Due to their low presence in mixtures and instability, the nature of the three potential forms present in the mixture could not be determined.

A summary of the forms of Nor-UDCA found during the polymorph screening study is presented in Table 4 und FIG. 4. The established conditions for the synthesis of pure Nor-UDCA (purification and recrystallization of the potassium salt of Nor-UDCA with subsequent precipitation of the free acid), however, only provides the physically pure and thermodynamically stable crystalline substance, i.e. Form A.

TABLE 1

Analytical procedures used in the polymorph screen (a) X-ray powder diffraction

| | |
|---|---|
| Equipment: | The plates were mounted on a Bruker GADDS diffractometer equipped with a Hi-Star area detector. |
| Calibration: | The XRPD platform was calibrated using Silver behenate for the long d-spacings end Corundum for the short d-spacings. |
| Data Collection: | Data collection was carried out at room temperature using monochromatic $CuK_\alpha$ radiation in the 2θ region between 1.5° and 41.5°. The diffraction pattern was collected in two 2θ ranges (1.5° ≤ 2θ ≤ 21.5° for the first frame and 19.5° ≤ 2θ ≤ 41.5° for the second) with an exposure time of 90 s for each frame. |

(b) Thermal analysis

| | |
|---|---|
| Differential scanning calorimetry: | Melting properties were obtained from DSC thermograms, recorded with a heat flux DCS822e instrument (Mettler-Toledo GmbH, Switzerland). The DSC8225e was calibrated for temperature and enthalpy with a small piece of indium (m.p. = 156.6° C.; ΔHf = 28.45 $Jg^{-1}$). The samples were heated in the DSC from 25° C. to 300° C., at a heating rate of 10° C./min. Dry $N_2$ gas, at a flow rate of 50 ml/min was used to purge the DSC equipment during measurement. |
| Thermogravimetric analysis: | Mass loss due to solvent or water loss from the crystals was determined by TGA/SDTA. Monitoring the sample weight, during heating in a TGA/SDTA851e instrument (Mettler-Toledo GmbH, Switzerland), resulted in a weight versus temperature curve. The TGA/SDTA851e was calibrated for temperature with indium and aluminium. The sample crucibles were heated in the TGA from 25 to 300° C. at a heating rate of 10° C./min. Dry $N_2$ gas was used for purging. |

(c) Thermogravimetric analysis/mass spectroscopy

A Thermostar GSD 301 T2 quadruple mass spectrometer (Pfeiffer Vacuum GmbH, Asslar) coupled with a quartz capillary to the TGA instrument was used to identify released gasses. The ultimate detection limit is $10^{-14}$ mbar, and sensitivity for Ar is 200 A/mbar. A multiple Ion Detection (MID) measurement was performed with a channeltron voltage of 950 V.

(d) Digital imaging and optical microscopy

Digital images were collected employing a Philips PCVC 840K CCD camera. Optical microscopy images were made using a Leica MZ9.5 stereomicroscope equipped with a Leica DC 300 digital camera.

(e) Dynamic vapour sorption

Moisture sorption isotherms were made using a DVS-1 system (Surface Measurement Systems, London, UK).

(f) HPLC/RI

| | |
|---|---|
| HPLC equipment: | Merck Amazon LC-01 LaChrom |
| Column: | Waters XBridge C18 (250 × 4.6 mm; 5 μm), T = 40° C. |
| Mobile phase: | Isocratic mode (ACN:MeOH:5 mM phosphate buffer pH 3 = 30:40:50 |
| RI-Detecter | Merck L-7490 |

TABLE 2

Solubility assessment results of Nor-UDCA

| Solvent | Solubility (mg/ml) | Form (by XRPD) |
|---|---|---|
| Pentane | <13 | Form A |
| Cyclohexane | <14 | Form A |
| N-Methyl-2-pyrrolidone | 404 | Form A |
| Tert-butylmethylether | <13 | Not determined |
| 1,4-Dioxane | 21 | Form A |
| 1,2-Dimethoxyethane | <14 | Form A |
| 2-Butanone | <14 | Form A |
| Dimethylsulfoxide | 207 | Not determined |
| Water | <12 | Form A |
| 1,2-Ethanediol | <14 | Not determined |
| 2,2,2-Trifluoroethanol | 21 | Form A |
| Chloroform | <14 | Form A |
| Methanol | 70 | Form A |
| Nitrobenzene | <13 | Form A |
| Dichlormethane | <13 | Form A |
| Acetone | <14 | Form A |
| Tetrhydrofurane | 41 | Form A |
| Nitromethane | <13 | Not determined |
| Toluene | <12 | Form A |
| Acetonitrile | <13 | Form A |

FIG. 1 shows the XRPD pattern of the starting material and the Form A obtained from different crystallization experiments. Note: Form A starting material in FIG. 1 means pure, polymorph, crystalline nor-ursodeoxycholic acid with defined particle size, used in the polymorph screening studies described.

TABLE 3

Single crystal data and structure refinement for Nor-UDCA Form A

| Identication code | Form A |
|---|---|
| Empirical formula | $C_{23}H_{38}O_4$ |
| Formula weight | 378.53 |
| T[K] | 297 (2) |
| λ [Å] | 0.71073 |
| Crystal system | Monoclinic |
| Space group | C2 |
| Unit cell dimensions | |
| a [Å] | 23.246 (3) |
| b [Å] | 11.197 (2) |
| c [Å] | 19.232 (4) |
| β [°] | 122.869 (13) |
| V [Å$^3$] | 4204.4 (13) |
| Z | 8 |
| $D_c$ [g/cm$^3$] | 1.196 |
| μ [mm$^{-1}$] | 0.080 |
| F(000) | 1664 |
| Crystal size [mm$^3$] | 0.45 × 0.35 × 0.25 |
| θ range for data collection | 3 → 32.6 |
| Reflections collected | 23586 |
| Independent reflections | 14414 [R$_{int}$ = 0.0541] |
| Completeness to θ = 32.6 | 96.6% |
| Max. and min. transmission | 0.9804 and 0.9651 |
| Data/restraints/parameters | 14414/1/505 |
| Goodness-of-fit on F$^2$ | 0.980 |
| Final R indices [I > 2σ(I)] | R1 = 0.0679, wR2 = 0.1194 |
| R indices (all data) | R1 = 0.1760, wR2 = 0.1513 |
| Absolute structure parameter | 0.2 (9) |

FIG. 2 deplete the crystal packing and H-bond scheme for nor-UDCA Form A. Note: Box indicates the single crystal packing of Nor-UDCA (Form A).

FIG. 3 depicts the molecular structure and atom numbering scheme by two symmetrically independent molecules of Nor-UDCA crystals.

TABLE 4

Summary of the forms of Nor-UDCA during the polymorph screening study

| Form/potential form and mixtures | Stability by XRPD | TGMS (%)/solvent loss Nature/remarks | Theoretical mass loss (%) | DSC endotherms (° C.) | HPLC/RI purity |
|---|---|---|---|---|---|
| Form A | Form A | Anhydrate | — | Endothermic event melt 249.5 | 99.96% |
| Form A plus 1 | Form A | — | — | — | — |
| Form A plus 2 | Form A plus 2 | Potential solvate 26.52% CHCl$_3$ 1.14 molecules CHCl$_3$ | 26.44 | Endothermic event 93 Exothermic event 105 Endothermic event melt 251.3 | — |
| Form B | Form A | — | — | — | — |
| Form C1 | Form A Form C$^{AS}$ | — Potential solvate 11.18% toluene 0.52 molecules toluene | — 11.24 | — Endothermic event 91.8 Endothermic event melt 250.9 | — |
| | Form A plus3* | — | — | — | — |
| Form C2 | Form A | — | — | — | — |

Notes:
$^{AS}$Anti-solvent experiment followed by cooling/evaporation
*Form C1 de-solvated and/or transformed during storage at ambient conditions FIG. 4 depicts the comparison of XRPD pattern of obtained new forms of Nor-UDCA and XRPD pattern of Form A. Note: Form A starting material in FIG. 4 means pure, polymorph, crystalline nor-ursodeoxycholic acid with defined pedicle size. Explanations of the XRPD patterns shown in FIG. 4:

Besides Form A, three potential mixtures of Form A with other forms were isolated. The presence of the new forms was indicated by the presence of additional peaks in the XRPD patterns of the solids, peaks that are not specific to the XRPD of Form A. Due to the fact that the XRPD analyses showed that the predominant form in the mixture is Form A, the potential mixtures were designated: Form A plus1, Form A plus2 and Form A plus3.

The mixture designated Form A plus1 was found upon completion of a cooling/evaporation experiment with anisole and methanol. Its XRPD pattern showed three additional peaks (next to the ones of Form A) at approx. 8.77°, 14.70° and 20.51° (2theta). The XRPD re-analyses of solids stored at ambient conditions in well and experimental vial showed that the mixture converted completely to Form A within 7 days.

The mixture designated Form A plus 2 was found upon completion of a slurry experiment at 5° C. with chloroform. The XRPD pattern of the solid shows five additional peaks at approx. 6.41°, 12.75°, 12.89°, 14.72° and 17.06° (2theta) in comparison with Form A. The XRPD re-analyses of solid stored at ambient conditions in well showed that the mixture converted completely to Form A within 11 days, but it was stable in experimental vial (within the same time interval).

The designated Form A plus3 mixture was identified after the conversion of Form C1 (anti-solvent experiments with 2,2,2-trifluoroethanol and toluene) stored at ambient conditions for 7 days. The XRPD pattern of the potential mixture Form A plus3 shows three additional peaks at 6.74°, 715° and 10.25° (2theta) in comparison with Form A.

Form B was identified upon completion of the cooling/evaporation experiment with 1,4-dioxane and tetrahydrofuran. The XRPD pattern of Form B is similar to that of Forms C1 and C2 in the sense that the main intense peaks common to Forms C1 and C2 are present in the XRPD of Form B as well. However, including Form B in the same isomorphic class of forms (as Form C1 and C2) was not straight forward possible due to the presence of the preferred orientation effects. The XRPD re-analyses of form B showed that it converted within 10 days to Form A upon storage in well and experimental vials at ambient conditions.

Form C1 was found in the cooling/evaporation experiments with p-Xylene and methanol. XRPD analyses of the solid stored at ambient conditions in the measuring well showed that the form converted to Form A within 7 days. Form C1 was also found in the anti-solvent experiments with 2,2,2-trifluoroethanol and toluene. Also in this case, the form converted to Form A within 7 days of storage in the well.

FIG. 5 separately shows the XRPD pattern of Form A. The polymorph is characterized by XRPD peaks at 11.9, 14.4, 15.3, 15.8, 18.8, 16.6±0.2° of 2-theta and having the general appearance as shown in FIG. 5.

Example 2

Chemical Purify of the Synthesized Nor-UDCA

The chemical impurity profile of the synthesized Nor-UDCA was evaluated by HPLC/RI. The method including the instrumental conditions are summarised in Table 5. The possible by-products from the synthesis are impurity A, impurity B, impurity C, impurity D, impurity E and impurity F. Impurity A is the starting material ursodeoxycholic acid (UDCA). impurity b is 3α,7β-dihydroxy-24-nor-5β-cholane-23amide, an intermediate formed by incomplete nitrile hydrolysis. Impurity C is Nor-Chenodeoxycholic acid (Nor-CDCA) which is a major impurity in the starting material UDCA. Impurity D is cholic acid (CA), another major impurity in the starting material UDCA. Impurity E is the formyl-protected UDCA which does not undergo the desired reaction. It is only a theoretically potential impurity as the formyl-protection groups will be cleaved by the alkaline treatment which as a result gives again impurity A. Impurity F is 3α,7β-dihydroxy-24-nor-5β-cholane-23-nitrile, another intermediate of the synthesis. The efficiency of the established purification methods is demonstrated by the results of the HPLC purity analyses of three batches of Nor-UDCA (see Table 6). Effective removal of the potentially known and unknown impurities by the recrystalization of the potassium salt of Nor-UDCA and subsequent precipitation of the free acid lead to chemically pure Nor-UDCA.

TABLE 5

| Purity method including instrumental conditions HPLC/RI | |
|---|---|
| Column: | Waters Symmetry C18 250 × 4.6 mm, 5 μm |
| Mobile phase: | 30 Acetonitrile |
| | 40 Methanol |
| | 50 5 mM Phosphate buffer pH 3.0 |
| Temperature: | 40° C. |
| Dectection: | Refractive index detector |

TABLE 5-continued

| Purity method including instrumental conditions HPLC/RI | |
|---|---|
| Flow rate: | 0.8 ml/min |
| Injection volumn: | 150 μl |

TABLE 6

| Results of purity determination of Nor-UDCA | | | |
|---|---|---|---|
| | Batch 40019721 | Batch 40019902 | Batch 40019898 |
| Impurity A | ≤0.03%[1] | ≤0.03% | ≤0.03% |
| Impurity B | ≤0.03% | ≤0.03% | ≤0.03% |
| Any other impurity | ≤0.03% | ≤0.03% | ≤0.03% |
| Sum of all impurities | ≤0.03% | ≤0.03% | ≤0.03% |

[1]Representing the limit of quantitation of the analytical procedure

Example 3

Particle Size of the Synthesised Nor-UDCA

The precipitation of the free acid leads to Nor-UDCA particles of a consistent and defined size distribution. Micronization by milling in order to control the crystal size of Nor-UDCA can be avoided. The results of the particle size measurement of three batches of Nor-UDCA demonstrate that the desired particle size of less than 10 μm can be obtained directly by the established conditions of precipitation (see Table 7).

TABLE 7

| Results of particle size determination of Nor-UDCA by laser diffraction (Equipment: Malvern Laser Diffraction Analyzer; Method: Dry; System details: Lense range 300 mm, beam length 10.00 mm) | | | |
|---|---|---|---|
| Particle size | Batch 40019721 | Batch 40019902 | Batch 40019898 |
| 1 μm < D(v, 0.5) < 8 μm | 6.4 μm | 6.7 μm | 5.4 μm |

SUMMARY

Presented here, is the formation and re-crystallization of the Nor-UDCA potassium salt from a mixture of 2-propanol and water followed by a precipitation of the free acid from a mixture of water and acetone. This purification method via the potassium salt proves to be very effective in removing both known impurities as well as unknown impurities. In conclusion, the process described is highly efficient to provide a chemically pure, single-polymorphic, crystalline preparation of Nor-UDCA with a defined particle size.

The invention claimed is:

1. A chemically pure polymorph of Nor-UDCA or of a pharmaceutically acceptable salt thereof, wherein the total amount of chemical impurities is less than 0.5%, at least 60% of the polymorph particles have a size <10 μm, and wherein said polymorph contains substantially no detectable amorphous Nor-UDCA.

2. The polymorph of claim 1, wherein the total amount of chemical impurities is less than 0.1%.

3. The polymorph of claim 2, wherein the total amount of chemical impurities is less than 0.05%.

4. The polymorph of claim 1, wherein said Nor-UDCA or pharmaceutically acceptable salt thereof is in its anhydrous form.

5. The polymorph of claim 1, containing no amorphous Nor-UDCA detectable by x-ray powder diffraction.

6. The polymorph of claim 5, containing no amorphous Nor-UDCA.

7. The polymorph of claim 1, having a volume-weighted average particle diameter D50 of less than 10 µm.

8. The polymorph of claim 1, having a volume-weighted average particle diameter D95 of less than 30 µm.

9. A pharmaceutical composition comprising the polymorph according to claim 1.

10. The pharmaceutical composition according to claim 9, which is formulated for oral, parenteral, subcutaneous, intravenous, intramuscular, nasal, topical or rectal administration.

11. The pharmaceutical composition according to claim 9, comprising one or more pharmaceutically acceptable excipients.

12. A method of treating cholestatic liver disease, non-alcoholic steato-hepatitis, alcoholic steato-hepatitis and arteriosclerosis by administering to a subject a pharmaceutical composition comprising a chemically pure polymorph of Nor-UDCA or of a pharmaceutically acceptable salt thereof, wherein the total amount of chemical impurities is less than 0.5%, at least 60% of the polymorph particles have a size <10 µm, and wherein said polymorph contains substantially no detectable amorphous Nor-UDCA.

13. The method of claim 12, wherein the cholestatic liver disease is selected from the group consisting of primary biliary cirrhosis (PBC), primary sclerosing cholangitis (PSC) and autoimmune hepatitis (AIH).

14. The method of claim 12, wherein said treating comprises treating arteriosclerosis.

15. The method of claim 12, wherein said treating comprises treating non-alcoholic steato-hepatitis.

16. The method of claim 12, wherein said treating comprises treating alcoholic steato-hepatitis.

17. A method for the preparation of a pure polymorph of Nor-UDCA or of a pharmaceutically acceptable salt thereof containing substantially no detectable amorphous Nor-UDCA, comprising:
   crystallizing the potassium salt of Nor-UDCA; and
   optionally dissolving the potassium salt in a solvent and acidifying the solution to obtain pure Nor-UDCA.

18. The method of claim 17, wherein said solvent is a mixture of water and acetone, and wherein said precipitation is carried out by acidifying the solution to have a pH in the range of 1 to 2.

19. The method of claim 17, further comprising:
   (a) converting a compound of formula (A)

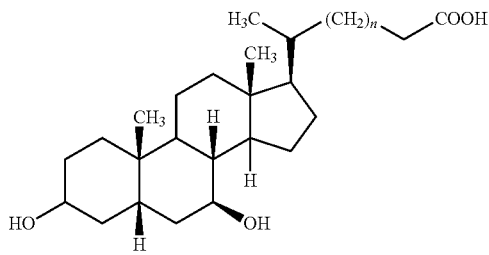

into a compound of formula (B)

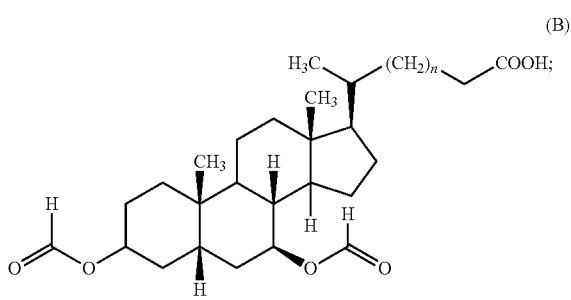

(b) converting the compound of formula (B) into a compound of formula (C)

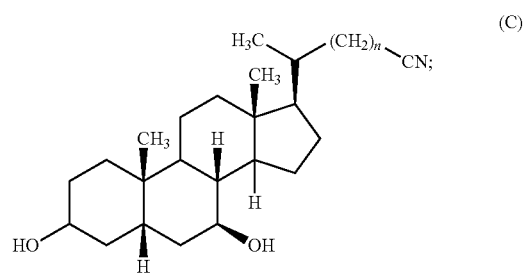

(c) converting the compound of formula (C) into a compound of formula (D) in crude form

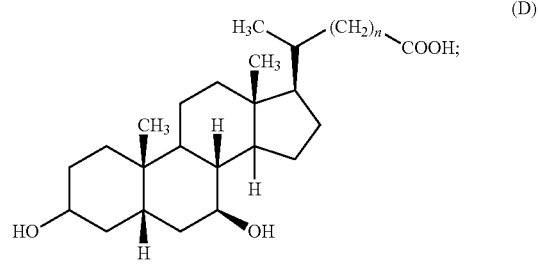

and
   (d) treating the compound of formula (D) in crude form with KOH under conditions to crystallize the potassium salt of Nor-UDCA;
   wherein n is 1.

20. The method of claim 17, characterized in that it does not comprise a milling step and/or a micronization step.

* * * * *